US00PP25105P2

(12) United States Plant Patent
Wood

(10) Patent No.: US PP25,105 P2
(45) Date of Patent: Nov. 25, 2014

(54) ***HYDRANGEA* PLANT NAMED 'SMHMLDD'**

(50) Latin Name: *Hydrangea macrophylla*
Varietal Denomination: SMHMLDD

(71) Applicant: Timothy D. Wood, Spring Lake, MI (US)

(72) Inventor: Timothy D. Wood, Spring Lake, MI (US)

(73) Assignee: Spring Meadow Nursery Inc., Grand Haven, MI (US)

( * ) Notice: Subject to any disclaimer, the term of this patent is extended or adjusted under 35 U.S.C. 154(b) by 0 days.

(21) Appl. No.: 13/987,718

(22) Filed: Aug. 23, 2013

(51) Int. Cl.
*A01H 5/00* (2006.01)

(52) U.S. Cl.
USPC ..... Plt./250

(58) Field of Classification Search
CPC ..... A01H 5/00
USPC ..... Plt./250
See application file for complete search history.

(56) References Cited

PUBLICATIONS

UPOV hit for *Hydrangea* plant named 'SMHMLDD'.*

* cited by examiner

*Primary Examiner* — Anne Grunberg
(74) *Attorney, Agent, or Firm* — C. A. Whealy

(57) ABSTRACT

A new and distinct cultivar of *Hydrangea* plant named 'SMHMLDD', characterized by its upright and mounded plant habit; strong and sturdy stems; dark green-colored leaves; large lacecap-type inflorescences with large soft pink-colored sterile flowers and red purple-colored fertile flowers; and reblooming habit.

2 Drawing Sheets

Botanical designation: *Hydrangea macrophylla.*
Cultivar denomination: 'SMHMLDD'.

BACKGROUND OF THE INVENTION

The present invention relates to a new and distinct *Hydrangea* plant, botanically known as *Hydrangea macrophylla* and hereinafter referred to by the name 'SMHMLDD'.

The new *Hydrangea* plant is a product of a planned breeding program conducted by the Inventor in Grand Haven, Mich. The objective of the breeding program was to develop new reblooming *Hydrangea* plants with strong stems and attractive flower coloration.

The new *Hydrangea* plant originated from a cross-pollination during the summer of 2007 of *Hydrangea macrophylla* 'Lynn', disclosed in U.S. Plant Pat. No. 20,019, as the female, or seed parent and *Hydrangea macrophylla* 'ES5', not patented, as the male, or pollen, parent. The new *Hydrangea* plant was discovered and selected by the Inventor as a single flowering plant from within the progeny of the stated cross-pollination in a controlled environment in Grand Haven, Mich. in 2009.

Asexual reproduction of the new *Hydrangea* plant by softwood cuttings in a controlled environment in Grand Haven, Mich. since July, 2009 has shown that the unique features of this new *Hydrangea* plant are stable and reproduced true to type in successive generations of asexual reproduction.

SUMMARY OF THE INVENTION

Plants of the new *Hydrangea* have not been observed under all possible environmental conditions and cultural practices. The phenotype may vary somewhat with variations in environmental conditions such as temperature and light intensity without, however, any variance in genotype.

The following traits have been repeatedly observed and are determined to be the unique characteristics of 'SMHMLDD'. These characteristics in combination distinguish 'SMHMLDD' as a new and distinct *Hydrangea* plant:

1. Upright and mounded plant habit.
2. Strong and sturdy stems.
3. Dark green-colored leaves.
4. Large lacecap-type inflorescences with large soft pink-colored sterile flowers and red purple-colored fertile flowers.
5. Reblooming habit.

Plants of the new *Hydrangea* differ from plants of the female parent, 'Lynn', in the following characteristics:

1. Plants of the new *Hydrangea* have larger inflorescences than plants of 'Lynn'.
2. Plants of the new *Hydrangea* have larger sterile flowers than plants of 'Lynn'.
3. Plants of the new *Hydrangea* have lighter pink-colored sterile flowers than plants of 'Lynn'.

Plants of the new *Hydrangea* differ from plants of the male parent, 'ES5', in the following characteristics:

1. Plants of the new *Hydrangea* have larger inflorescences than plants of 'ES5'.
2. Plants of the new *Hydrangea* have larger sterile flowers than plants of 'ES5'.

Plants of the new *Hydrangea* can be compared to plants of *Hydrangea serrata* 'Mak20', disclosed in U.S. Plant patent application Ser. No. 13/573,841. In side-by-side comparisons, plants of the new *Hydrangea* differed primarily from plants of 'Mak20' in the following characteristics:

1. Plants of the new *Hydrangea* had larger inflorescences than plants of 'Mak20'.

2. Plants of the new *Hydrangea* had larger sterile flowers than plants of 'Mak20'.
3. Plants of the new *Hydrangea* had lighter pink-colored sterile flowers than plants of 'Mak20'.

BRIEF DESCRIPTION OF THE PHOTOGRAPHS

The accompanying colored photographs illustrate the unique appearance of the new *Hydrangea* plant showing the colors as true as it is reasonably possible to obtain in colored reproductions of this type. Colors in the photographs may differ from the color values cited in the detailed botanical description which accurately describe the colors of the new *Hydrangea* plant.

The photograph on the first sheet comprises a side perspective view of a typical flowering plant of 'SMHMLDD'.

The photograph on the second sheet is a close-up view of a typical inflorescence of 'SMHMLDD'.

DETAILED BOTANICAL DESCRIPTION

Plants used for the aforementioned photographs and the following description were grown during the summer in two-gallon containers in an outdoor nursery in Grand Haven, Mich. and under cultural practices typical of commercial *Hydrangea* production. Plants of the new *Hydrangea* were two years old when the photographs and description were taken. In the following description, color references are made to The Royal Horticultural Society Colour Chart, 2001 Edition, except where general terms of ordinary dictionary significance are used.

Botanical description: *Hydrangea macrophylla* 'SMHMLDD'.

Parentage:

*Female, or seed, parent.*—*Hydrangea macrophylla* 'Lynn', disclosed in U.S. Plant Pat. No. 20,019.

*Male, or pollen, parent.*—*Hydrangea macrophylla* 'ES5', not patented.

Propagation:

*Type cutting.*—By softwood cuttings.

*Time to initiate roots, summer.*—About 15 days at temperatures of about 24° C.

*Time to produce a rooted young plant, summer.*—About 40 days at temperatures of about 24° C.

*Root description.*—Fine and thick; white and brown in color.

*Rooting habit.*—Freely branching; dense.

Plant description:

*Plant form and growth habit.*—Perennial deciduous shrub; upright and mounded plant habit; inverted triangle; strong and sturdy lateral branches; freely branching habit with about seven lateral branches per plant; vigorous growth habit.

*Plant height.*—About 36 cm.

*Plant diameter or area of spread.*—About 58 cm.

*Lateral branches.*—Length: About 21 cm. Diameter: About 5 mm. Internode length: About 4.5 cm. Texture: Smooth, glabrous. Strength: Strong, sturdy. Color: Close to 145B; with development becoming closer to 145A.

Leaf description:

*Arrangement.*—Opposite, simple.

*Length.*—About 17.6 cm.

*Width.*—About 8.5 cm.

*Shape.*—Ovate.

*Apex.*—Acuminate.

*Base.*—Obtuse.

*Margin.*—Serrulate.

*Texture, upper and lower surfaces.*—Smooth, glabrous.

*Venation pattern.*—Pinnate.

*Color.*—Developing leaves, upper surface: Close to 137B. Developing leaves, lower surface: Close to 137C. Fully expanded leaves, upper surface: Close to 137A; venation, close to 145B. Fully expanded leaves, lower surface: Close to 137C; venation, close to 145C.

*Petioles.*—Length: About 2 cm. Diameter: About 5 mm. Texture, upper and lower surfaces: Smooth, glabrous. Color, upper surface: Close to 145C. Color, lower surface: Close to 145B.

Flower description:

*Flower type and habit.*—Single sterile and fertile flowers arranged on large terminal lacecap-type cymes; flowers face upright or outwardly.

*Fragrance.*—None detected.

*Natural flowering season.*—Plants flower throughout the summer in Grand Haven, Mich.; plants continue to rebloom during this period.

*Flower longevity, sterile flowers.*—Flowers last about one to two months on the plant; flowers persistent.

*Quantity of flowers.*—Freely flowering habit; about 130 fertile flowers and about 15 sterile flowers per inflorescence.

*Inflorescence height.*—About 8 cm.

*Inflorescence diameter.*—About 17 cm.

*Flower diameter, fertile flowers.*—About 1 cm.

*Flower depth (height), fertile flowers.*—About 1 cm.

*Flower diameter, sterile flowers.*—About 6.3 cm.

*Flower depth (height), sterile flowers.*—About 5 mm.

*Flower buds, fertile flowers.*—Length: About 6 mm. Diameter: About 5 mm. Shape: Obovate. Color: Close to 65C.

*Flower buds, sterile flowers.*—Length: About 5 mm. Diameter: About 4 mm. Shape: Obovate. Color: Close to 157A.

*Petals, fertile flowers only.*—Arrangement: Five in a single whorl. Length: About 5 mm. Width: About 3 mm. Shape: Ovate. Apex: Acute. Base: Obtuse. Margin: Entire. Texture, upper and lower surfaces: Smooth, glabrous. Color: When opening, upper surface: Close to 74C. When opening, lower surface: Close to 75B. Fully opened, upper surface: Close to 74C. Fully opened, lower surface: Close to 84C.

*Sepals, fertile flowers.*—Quantity per flower: Five in a single whorl. Length: About 1 mm. Width: About 1 mm. Shape: Subulate. Apex: Acute. Base: Cuneate. Margin: Entire. Texture, upper and lower surfaces: Smooth, glabrous. Color: When opening, upper and lower surfaces: Close to 145C. Fully opened, upper and lower surfaces: Close to 138D.

*Sepals, sterile flowers.*—Quantity per flower: Five in a single whorl. Length: About 4 cm. Width: About 3.5 cm. Shape: Ovate. Apex: Acute. Base: Attenuate. Margin: Entire. Texture, upper and lower surfaces: Smooth, glabrous. Color: When opening, upper surface: Close to 73C. When opening, lower surface: Close to 73D. Fully opened, upper surface: Close to 73D; towards the base, close to 73B. Fully opened, lower surface: Close to 69C.

*Pedicels, fertile flowers*.—Angle: About 35° to 55° from inflorescence axis. Strength: Strong, sturdy. Length: About 1 cm. Diameter: About 3 mm. Texture: Pubescent. Color: Close to 70C.

*Pedicels, sterile flowers*.—Angle: About 35° to 45° from inflorescence axis. Strength: Strong, sturdy. Length: About 2 cm. Diameter: About 2 mm. Texture: Pubescent. Color: Close to 159B.

*Reproductive organs, fertile flowers*.—Stamens: Quantity per flower: About ten. Filament length: About 1.2 cm. Filament color: Close to 74D. Anther shape: Oblong. Anther length: About 1 mm. Anther color: Close to 155A and 202B. Pollen amount: None observed. Pistils: Pistil quantity per flower: About four. Pistil length: About 6 mm. Stigma shape: Oblong. Stigma color: Close to 67B. Style length: About 3 mm. Style color: Close to 67B. Ovary color: Close to 145D.

*Reproductive organs, sterile flowers*.—Stamens: Quantity per flower: About eight. Filament length: About 3 mm. Filament color: Close to 73A. Anther shape: Round. Anther length: About 1 mm. Anther color: Close to 155A and 202B. Pollen amount: None observed. Pistils: Pistil quantity per flower: About three. Pistil length: About 5 mm. Stigma shape: Round. Stigma color: Close to 58B. Style length: About 2 mm. Style color: Close to 57C. Ovary color: Close to 159B.

*Seeds*.—Quantity per inflorescence: Numerous. Size: Less than 0.1 mm by less than 0.1 mm. Color: Brown.

Disease & pest resistance: Plants of the new *Hydrangea* have not been observed to be resistant to pathogens and pests common to *Hydrangea* plants.

Temperature tolerance: Plants of the new *Hydrangea* have been shown to be tolerant to temperatures ranging from about −27° C. to about 37° C.

It is claimed:

1. A new and distinct *Hydrangea* plant named 'SMH-MLDD' as illustrated and described.

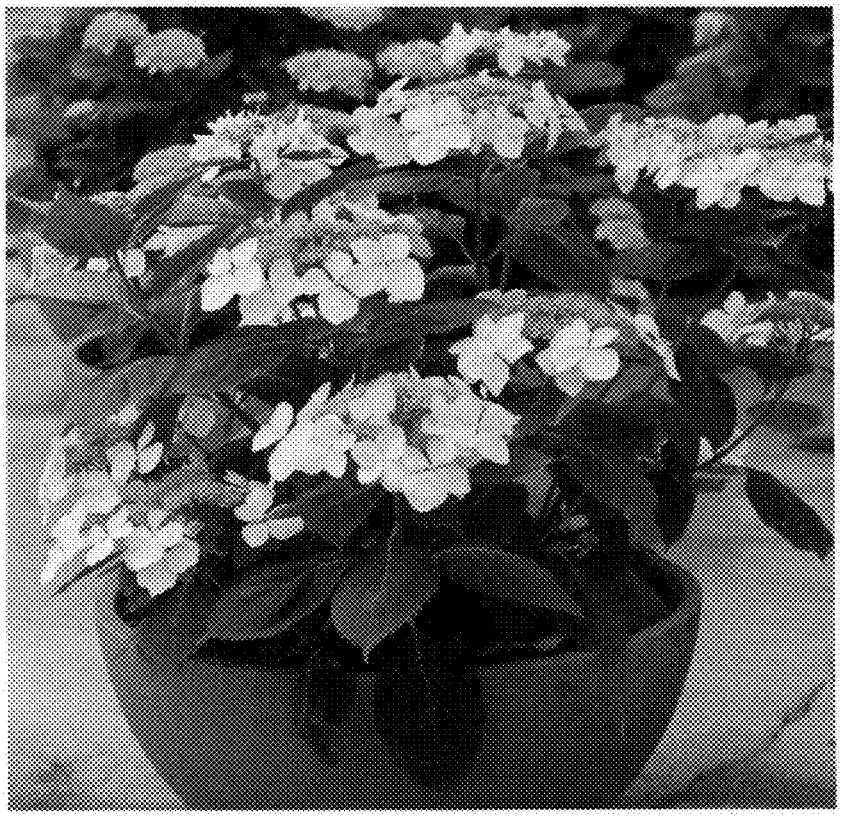

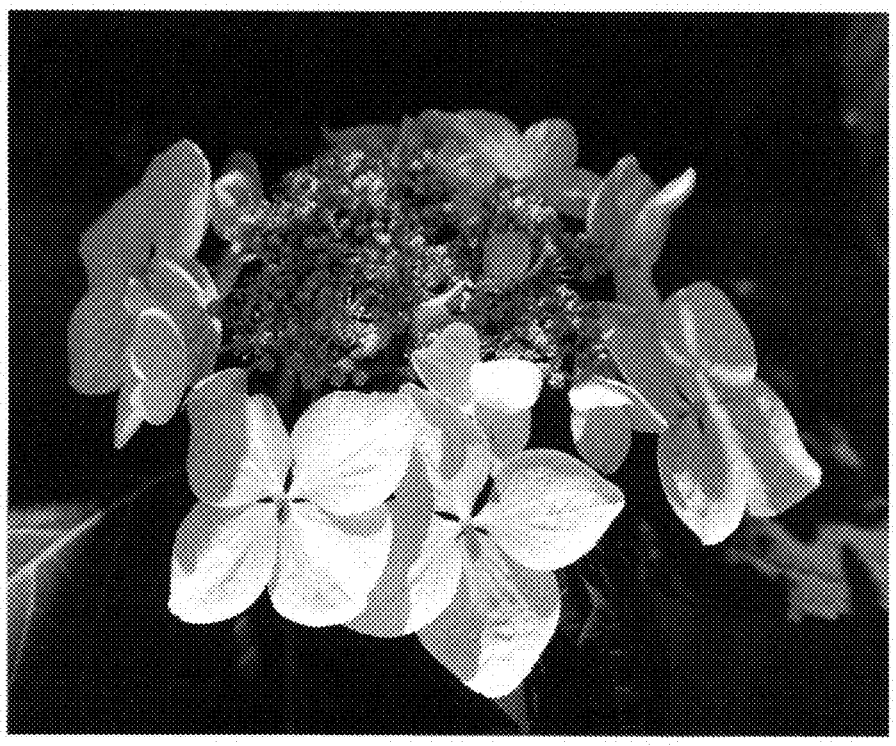

* * * * *